(12) United States Patent
Wolf

(10) Patent No.: US 8,029,818 B2
(45) Date of Patent: Oct. 4, 2011

(54) METHOD OF BLUNTING THE POSTPRANDIAL GLYCEMIC RESPONSE TO A MEAL

(75) Inventor: Bryan W. Wolf, Johnstown, OH (US)

(73) Assignee: Abbott Laboratories, Abbott Park, IL (US)

( * ) Notice: Subject to any disclaimer, the term of this patent is extended or adjusted under 35 U.S.C. 154(b) by 1241 days.

(21) Appl. No.: 10/157,644

(22) Filed: May 29, 2002

(65) Prior Publication Data

US 2003/0017191 A1    Jan. 23, 2003

Related U.S. Application Data

(60) Provisional application No. 60/294,901, filed on May 31, 2001.

(51) Int. Cl.
*A61K 9/20* (2006.01)
*A61K 31/70* (2006.01)

(52) U.S. Cl. ........ 424/439; 424/441; 424/451; 424/464; 514/23; 514/866

(58) Field of Classification Search .................. 424/421, 424/439, 440, 441, 451, 464; 514/23, 866
See application file for complete search history.

(56) References Cited

U.S. PATENT DOCUMENTS 5,470,839 A   11/1995 Laughlin et al.
5,843,921 A * 12/1998 Kaufman .................. 514/60

FOREIGN PATENT DOCUMENTS

EP    0 265 772 B1   12/1992

OTHER PUBLICATIONS

Webster's ninth New Collegiate Dictioney, 1986, Merriam-Webster Inc., Ninth Edition, p. 1114.*
Lundstrom et al, The Healing Handbook for Persons with Diabetes, 1995-1999.*
http://www.,minitemaid.com/mm-products/ Minute Maid Product Information (1946).*
Matthew et al, Sugar Content of Selected Foods: Individual and Total Sugars, United States Department of Agriculture, Human Nutrition Information Service, Home Economics Report, No. 48, Sep. 1987, pp. 1-2, 17-19.*
Moore et al (Acute Fructose Administration Decreases the Glycemic Response to an Oral glucose Test in Normal Adults, the Journal of Clinical Endocrinology & Metabolism, vol. 85, No. 12, 4515-4519.).*
Anderson et al, Metabolic effects of fructose supplementation in diabetic individuals, Diabetes Care, May 1989; 12(5): 337-44.*
Uusitupa, Fructose in the diabetic diet, American Journal Nutrition, Mar. 1994; 59 (3): 753-757.*

(Continued)

*Primary Examiner* — Lakshmi Channavajjala
(74) *Attorney, Agent, or Firm* — Mark R. Engle; Sandra E. Weida; Mimi C. Goller

(57) ABSTRACT

The present invention relates to a method for reducing the postprandial glycemic excursion to carbohydrates by feeding supplemental fructose prior to the carbohydrate challenge. The unit does of fructose required to blunt the postprandial glycemic excursion is from about 2 grams to about 30 grams fructose. The fructose source is consumed from about 10 to about 90 minutes before a meal.

12 Claims, 4 Drawing Sheets

Plasma glucose response of 31 volunteers to instant mashed potatoes ñ 10 g fructose given at different times Values represent mean ñ SEM. To convert glucose mg/dl to mmol/L, multiply mg/dl by 0.0555

OTHER PUBLICATIONS

Van de Ven et al., "Effects of liquid preloads with different fructose/fibre concentrations on subsequent food intake and ratings of hunger in women," Appetite, vol. 23, No. 2, pp. 139-146 (1994) (abstract only).*

Van de Ven et al., "Effects of liquid preloads with different fructose/fibre concentrations on subsequent food intake and ratings of hunger in women," Appetite, vol. 23, No. 2, pp. 139-146 (1994) (full document).*

Tremble et al., "Is continued weight gain inevitable in type 2 diabetes mellitus?", J R Soc Health, Dec. 1999; 119 (4):235-9.*

Distinctions among three sugars in their effects on gastric emptying and satiety Moran and McHugh Am J Physiol Regul Integr Comp Physiol.1981; 241: 25-30.*

Rodin, Comparative effects of fructose, aspartame, glucose, and water preloads on calorie and macronutrient intake, Am J Clin Nutr 1990; 51:428-35.*

Araya et al, Arch Latinoam Nutr, Mar. 1995; 45(1):25-30.*

Gerrits et al, Am. J. Clin. Nutr. 1993, 58 suppl): 796S-9S.* http://www.emedicine.com/emerg/topic134.htm (Votey, Diabetes Mellitus, Type 2—A Review).*

Araya et al, [Effect of protein and carbohydrate preloads on food and energy intakes in preschool children with different nutritional status]. Arch. Latinoam Nutr., Mar. 1995; 45(1), abstract and a full translation attached to this action.*

Resource® Diabetic, 1995 Clinical Products Division, Sandoz Nutrition Company.

Compelling Comparisons Glucerna®, 1996 Ross Products Division, Abbott Laboratories.

Choice*dm*™, 1997 Mead Johnson & Company.

Matthews, et al., Sugar Content of Selected Foods: Individual and Total Sugars, United States Department of Agriculture, Human Nutrition Information Service, Home Economics Report, No. 48, Sep. 1987, pp. 1-2, 17-19.

Ensure® Nutrition and Energy Bars, Ross Products Division, Abbott Laboratories, Dec. 2001.

*All items listed below can be found on* www.ross.com Copyright 1996.

Ensure Plus®, Ross Products Division, Abbott Laboratories (Jun. 24, 2004).

Ensure® Nutrition and Energy Bars, Ross Products Division, Abbott Laboratories, (Jun. 24, 2004).

Glucema® Snack Bars, Ross Products Division, Abbott Laboratories (Jun. 24, 2004).

Glucema® Shake, Ross Products Division, Abbott Laboratories (Jun. 24, 2004).

Glucema®, Ross Products Division, Abbott Laboratories (Jun. 24, 2004).

\* cited by examiner

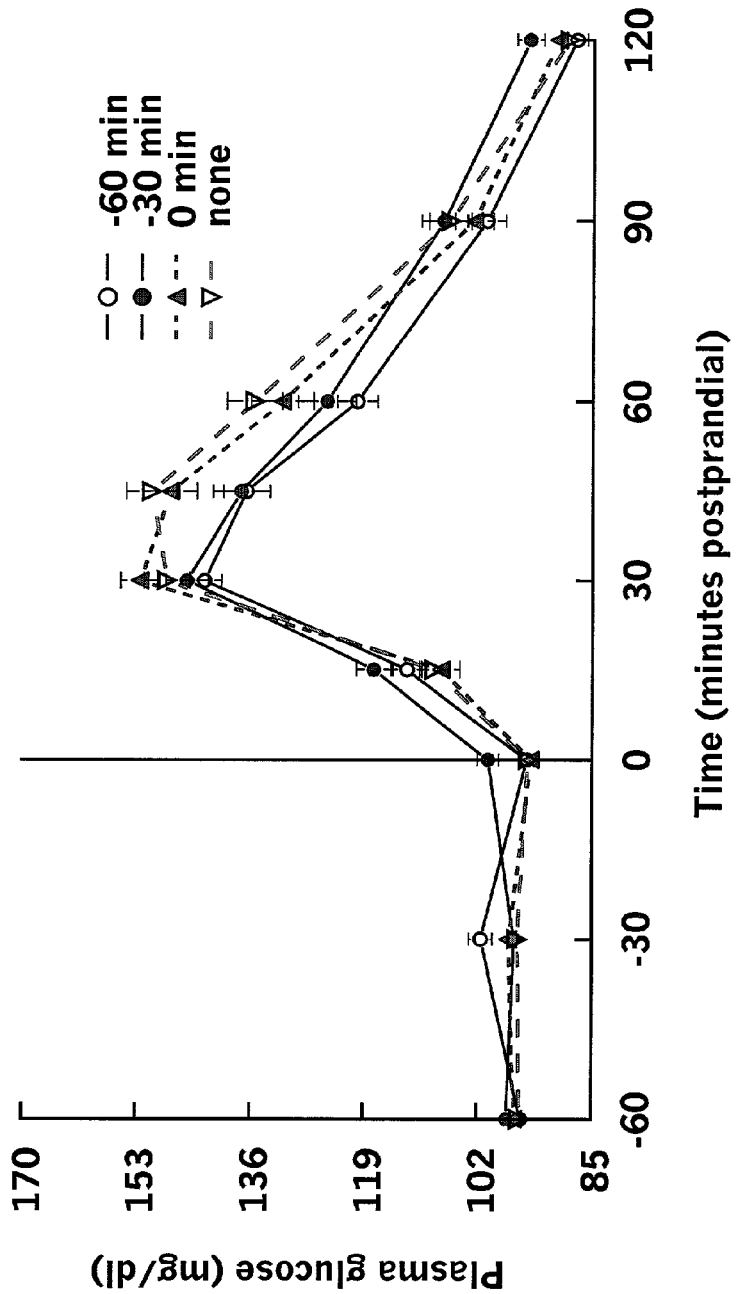

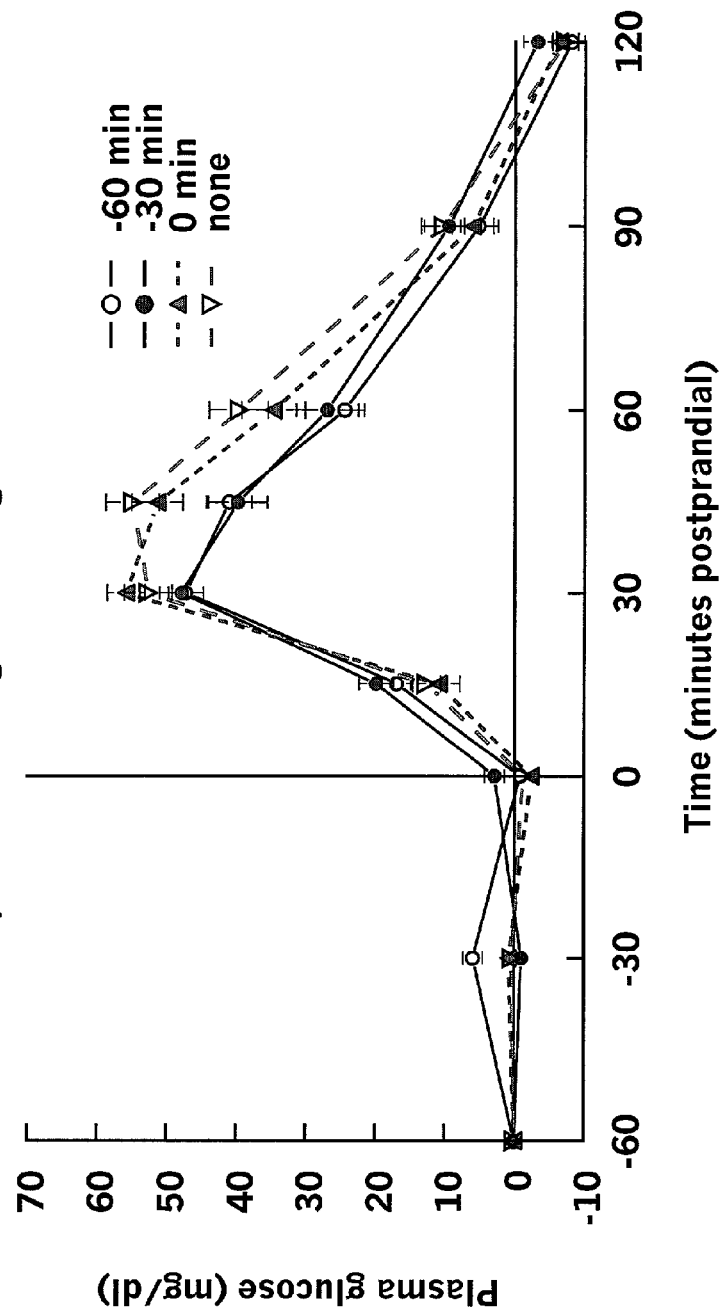

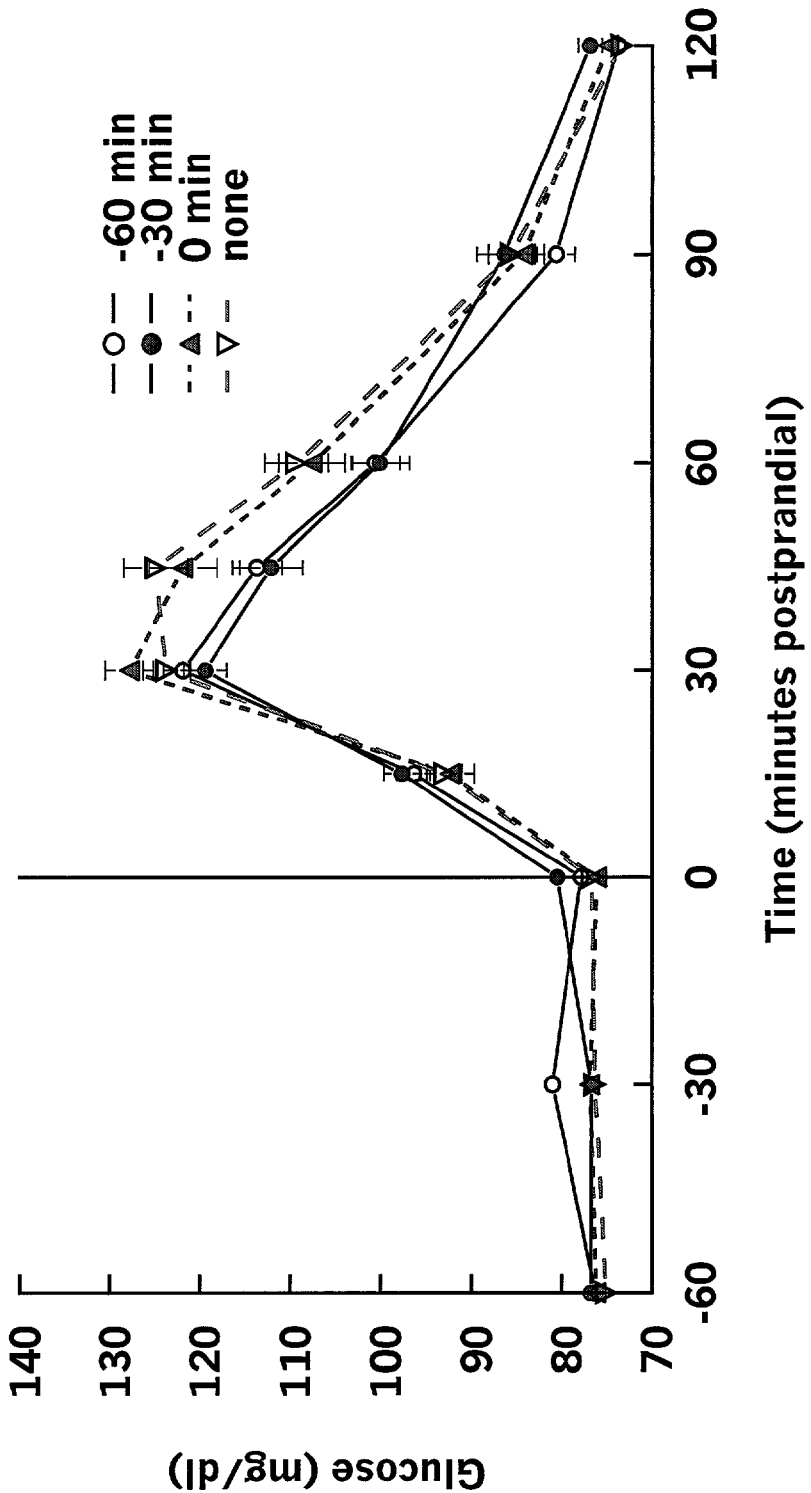

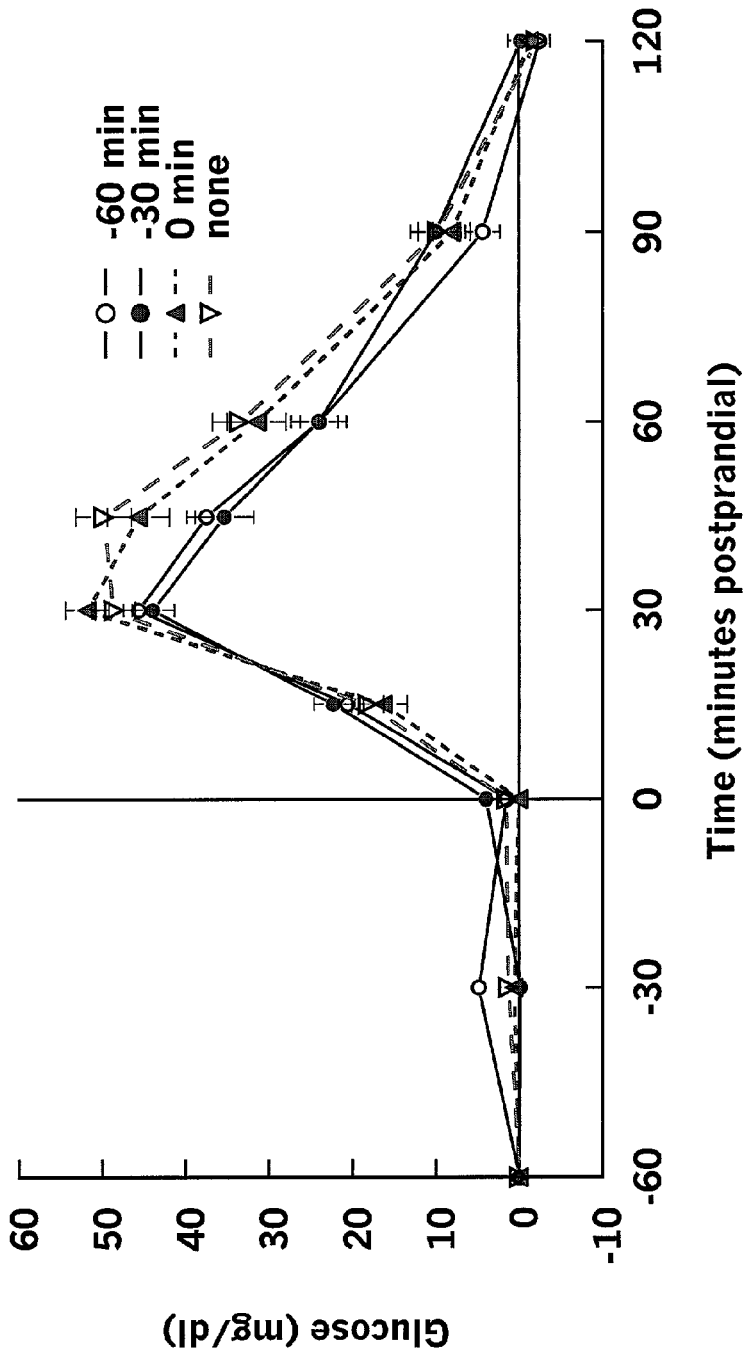

METHOD OF BLUNTING THE POSTPRANDIAL GLYCEMIC RESPONSE TO A MEAL

CROSS REFERENCE

This application is a continuation-in-part of U.S. Patent Application Ser. No. 60/294,901, which was filed on May 31, 2001.

TECHNICAL FIELD

The present invention relates to a method for reducing the postprandial glycemic excursion by feeding supplemental fructose prior to the carbohydrate challenge and to its use in the dietary management of diabetics.

INTRODUCTION

The control of blood glucose in people with diabetes mellitus is of paramount importance for the long-term management of this disease. While intensive treatment with insulin or oral glucose-lowering agents is of great benefit, they are associated with an increased risk of hypoglycemia and weight gain. The concomitant use of diet as adjunctive therapy for the management of blood glucose further enhances the quality of life and reduces the risk of hypoglycemia and weight gain in people with diabetes. Furthermore, nutritional management should be the first mode of treatment for people with insulin resistance or early stage type 2 diabetes mellitus as well as a preventative therapy for high-risk populations (e.g., obese and first degree relatives of people with type 2 diabetes mellitus).

American Diabetes Association (ADA) guidelines emphasize individualization of diet strategies. The purpose is to achieve optimal glycemic and metabolic control by varying the proportion of calories provided by the macronutrients. The proportion selected depends on goals for glycemic control, dietary preferences and response to the diet.

The ADA currently recommends a diet in which protein is the same as that for the general population and accounts for 10% to 20% of total calories. With protein contributing 10% to 20% of the total calories, 80% to 90% of the total calories remain to be distributed between carbohydrate and fat. The carbohydrate/fat mix is individualized according to dietary preference, treatment goals, metabolic control and the presence of other medical conditions. However, the ADA does make a recommendation for the various types of fat in the diet. Specifically, saturated fat should contribute less than 10% of total calories, and polyunsaturated fat contributing no more than 10% of total calories. The remainder of fat calories should come from monounsaturated fat and the daily intake of cholesterol should be limited to less than 300 mg. The recommendation for fiber intake is the same as for the general public with approximately 20 to 35 g/day of dietary fiber from a variety of food sources. The micro nutrient requirements of otherwise healthy persons with diabetes mellitus will likely be met by consuming the amounts suggested by the Reference Daily Intakes (RDIs). Individuals considered at risk for micronutrient deficiencies should be evaluated to determine if supplementation is necessary. Because fructose and sucrose intake have been shown to cause hypertriacylglycerolemia and hypercholesterolemia in rats and humans, nutritional recommendations have been made to avoid supplementation of simple sugars to the diabetic diet.

Products designed as nutritionals for the person with diabetes are commercially available and typically include fructose as a sweetener. These nutritional products are typically liquids or in a solid form such as nutritional bars and baked goods.

Glucerna® (Ross Products Division of Abbott Laboratories, Columbus Ohio) is a liquid nutritional with fiber for patients with abnormal glucose tolerance. Sodium and calcium caseinates make up 16.7% of total calories as protein; maltodextrin, soy polysaccharide and fructose make up 34.3% of total calories as carbohydrate; and high oleic safflower oil and canola oil make up 49% of total calories as fat. Soy polysaccharide contributes 14.1 g/1000 ml of total dietary fiber. The RDI for vitamins and minerals is delivered in 1422 kcals. The product also contains the ultra trace minerals selenium, chromium and molybdenum and the conditionally essential nutrients carnitine and taurine.

Resource® Diabetic (Sandoz Nutrition Corporation, Berne, Switzerland) is a complete liquid formula with fiber specifically designed for persons with type 1 and type 2 diabetes and for persons with stress-induced hyperglycemia. Sodium and calcium caseinates, and soy protein isolate make up 24% of total calories as protein; hydrolyzed corn starch and fructose make up 36% of total calories as carbohydrate; and high oleic sunflower oil and soybean oil make up 40% of total calories as fat. Partially hydrolyzed guar gum contributes 3.0 g/8 fl. oz. of total dietary fiber. The RDI for vitamins and minerals is delivered in 2000 kcals. The product also contains the ultra trace minerals selenium, chromium and molybdenum and the conditionally essential nutrients carnitine and taurine.

Ensure® Glucerna® Shake (Ross Products Division of Abbott Laboratories, Columbus Ohio) is an oral supplement specifically designed for people with diabetes. Sodium and calcium caseinates and soy protein isolate make up 18% of total calories as protein; maltodextrin, fructose, maltitol, soy polysaccharide and FOS make up 47% of total calories as carbohydrate; and high oleic safflower oil and canola oil make up 35% of total calories as fat. Soy polysaccharide and fructooligosaccharides (FOS) contribute 3.0 g/8 fl. oz. of total dietary fiber. At least 25% of the DV for 24 key vitamins and minerals are delivered in 8 fl. oz. The product also contains the ultra trace minerals selenium, chromium and molybdenum.

Ensure®Glucerna® Snack Bars (Ross Products Division of Abbott Laboratories, Columbus Ohio) are complete, balanced nutritional bars designed specifically for people with diabetes. Soy protein, rice protein, corn protein and milk and cocoa (from the coating) make up 17% of total calories as protein; high fructose corn syrup, honey, microencapsulated guar gum, rice starch, maltodextrin, soy polysaccharide, glycerin, microcrystalline cellulose, fructooligosaccharides (FOS) and maltitol (from the coating) make up 57% of total calories as carbohydrate; and partially hydrogenated soy and cottonseed oils, high oleic safflower oil and canola oil make up 26% of total calories as fat. Microencapsulated guar gum, soy polysaccharide, microcrystalline cellulose, FOS and resistance starch contribute 4 g total dietary fiber per 1.34 oz bar. One bar provides at least 15% of the DV for 24 key vitamins and minerals. The product also contains the ultra trace minerals selenium, chromium and molybdenum and the conditionally essential nutrient m-inositol.

Choice Dm® Bar (Mead Johnson & Company, Evansville, Ind.) is a nutritional bar with fiber, antioxidants and 24 essential vitamins and minerals for people with diabetes. Calcium caseinate, soy protein isolate, whey protein concentrate, toasted soybeans, soy nuggets (soy protein isolate, rice flour, malt, salt) and peanut butter make up 17.1% of total calories as protein; lactose, fructose, sugar, dextrose, honey, maltodextrin, rice syrup, sorbitol and peanut flour make up 54.3% of total calories as carbohydrate; and palm kernel oil and canola oil make up 28.9% of total calories as fat.

Typically, the commercial nutritionals are designed as meal replacements and include all the macro and micronutrients required of a meal replacement. These nutritionals typically utilize multiple sources of carbohydrate that are absorbed at different rates to control the glycemic response to the nutritional. While the nutritionals are handy for a busy schedule when it is not practical to prepare a meal, many diabetics prefer to eat "normal" food and do not want to routinely consume their entire meal out of a can. There is clearly a need for an easy method to blunt the glycemic response of a meal composed of "normal" food.

SUMMARY OF THE INVENTION

The nutritive sweetener, fructose, in itself is a dietary carbohydrate source with a low postprandial glycemic excursion. Because of its reduced glycemic response, fructose is an ideal carbohydrate for use in the dietary control of postprandial glycemia in people with diabetes mellitus. However, because fructose intake levels greater than 17% of total Kcal have been shown to cause hypertriacylglycerolemia and hypercholesterolemia in rats and humans, dietary recommendations for the diabetic have been made to avoid high intakes of simple carbohydrates, especially fructose.

The inventors discovered that low amounts of supplemental fructose when given along with a meal glucose tolerance test had no effect on the postprandial glycemic response. However, when a low dose of fructose was given prior to the meal tolerance test, fructose reduced the postprandial glycemic response.

The present invention relates to a method for reducing the postprandial glycemic excursion to carbohydrates by feeding supplemental fructose prior to the carbohydrate challenge. The unit does of fructose required to blunt the postprandial glycemic excursion is from about 2 grams to about 30 grams fructose, preferably from about 5 to about 15 grams of fructose, more preferably about 10 grams of fructose. The fructose source is consumed from about 10 to about 90 minutes before a meal, preferably from about 15 to about 75 minutes before a meal, more preferably from about 30 to about 60 minutes before a meal.

The source of fructose may be any food grade fructose source such as sucrose, maltitol, high fructose corn syrup, honey, fruit, fruit juice, liquid fructose, powder fructose and crystalline fructose.

The fructose dose may be in any suitable form such as a tablet, caplet, lozenge, powder, crystal, fruit, syrup, candy and liquid.

The method may be used for nutritional management of persons with diabetes, for people with insulin resistance as well as a preventative therapy for high-risk populations (e.g., obese and first degree relatives of people with type 2 diabetes mellitus).

DESCRIPTION OF THE DRAWINGS

FIG. 1. Plasma glucose response of 31 volunteers to instant mashed potatoes ±10 g fructose given at different times.

FIG. 2. Change in plasma glucose response of 31 volunteers to potatoes ±10 g fructose given at different times.

FIG. 3. Whole blood glucose response of 30 volunteers to instant mashed potatoes ±10 g fructose given at different times.

FIG. 4. Change in capillary blood glucose response of 30 volunteers to potatoes ±10 g fructose given at different times.

DETAILED DESCRIPTION OF THE INVENTION

As used herein:
a. "glycemic index" (GI) is calculated by dividing the blood glucose incremental area under the curve (AUC) of the test food by the blood glucose incremental AUC of the reference food and multiplying by 100, where the carbohydrate content of test and reference foods are the same. The reference food is typically glucose or white bread, which has the standard GI of 100.
b. the terms "fructose" and "source of fructose" are used interchangeably and refer to the actual fructose content in a carbohydrate source.
c. any reference to a numerical range in this application should be construed as an express disclosure of every number specifically contained within that range and of every subset of numbers contained within that range. Further, this range should be construed as providing support for a claim directed to any number, or subset of numbers in that range. For example, a disclosure of 1-10 should be construed as supporting a range of 2-8, 3-7, 5, 6, 1-9, 3.6-4.6, 3.5-9.9, 1.1-9.9, etc The present invention relates to a method of feeding fructose to a person prior to a carbohydrate challenge, which significantly reduces the postprandial glycemic excursion to that challenge. As described in Example I, the inventors surprising discovered that 10 g supplemental fructose when given with a meal glucose tolerance test (50 g carbohydrate from instant mashed potatoes) had no effect on the postprandial glycemic response. However, when 10 g of fructose were given 30 or 60 minutes before the meal tolerance test, fructose reduced the postprandial glycemic response.

The amount of fructose required to blunt the postprandial glycemic excursion is from about 2 grams to about 30 grams, preferably from about 5 to about 15 grams of fructose, more preferably about 10 grams of fructose.

Any fructose source suitable for human consumption may be utilized in the instant invention. Examples of typical fructose sources include sucrose, maltitol, high fructose corn syrup, honey, fruit, fruit juice, liquid fructose, powder fructose and crystalline fructose. Examples of suitable fruit and fruit juices include apple, grape, orange, grapefruit, pear and watermelon.

Fructose is found in fruits and honey. More typically, commercially available fructose is produced by well known enzymatic conversion of saccharides to fructose. The fructose content of various sources is listed in Table 1 below.

TABLE 1

Carbohydrate profile of several fructose sources*

| % dry basis | fructose | high fructose corn syrup (representative profiles) | honey |
|---|---|---|---|
| fructose | 99.5 | 42 | 55 | 49 |
| glucose | 0.5 | 52 | 41 | 40 |
| maltose | 0 | 3 | 2 | 9 |
| higher saccharides | 0 | 3 | 2 | 2 |

*Fructose and corn syrup data from Cargill, Minneapolis, Minnesota product information sheets, honey values from National Honey Board, San Francisco, California Commercial high fructose corn syrup is available with various levels of fructose. The high fructose corn syrup profiles listed in Table 1 represent typical commercially available high fructose corn syrup, with fructose levels at 42% and 55% of the corn syrup, respectively. Typical values for fructose sources of different fruit may be found in Human Nutrition Information Service (1987) Sugar content of selected foods: Individual and total sugars. (Home Economics Research Report no. 48, USDA, Washington, D.C.) Examples of appropriate fruits include a raw apple (3¼ inch diameter) which typically contains 10.5 gm fructose and 4.6 gm of sucrose; a Bartlett pear (2½ inch diameter) typically contains 10.6 mg fructose and 3 gm of sucrose; and grape juice reconstituted frozen concentrate (8 fl. oz.) typically contains 11 gm of fructose. One knowledgeable in the art would be able to select the appropriate type and amount of fruit or fruit juice to serve as a source of fructose.

Any reference in this application to a quantity of fructose should be understood as referring to the actual fructose content within the carbohydrate source. For example, 100 gm of the honey in Table 1 would provide 49 gm of fructose. One skilled in the art can readily calculate how much of a carbohydrate source is required to deliver the desired amount of fructose.

Fructose may be indirectly provided by feeding maltitol or sucrose to the subject. Sucrose is hydrolyzed and absorbed in the small intestine as glucose and fructose. Maltitol (glucose alpha-1,4 sorbitol) is hydrolyzed and absorbed in the small intestine as glucose and sorbitol. Sorbitol is dehydrogenated (via sorbitol dehydrogenase) in the liver to fructose. Sorbitol alone is not a suitable indirect source of fructose, because it is malabsorbed from the small intestine.

Commercial sources for fructose are readily available and known to one practicing the art. For example, various high fructose corn syrups are available from Cargil in Minneapolis, Minn. Liquid and powder fructose is available from A. E. Staley in Decatur, Ill. Honey, fruit and fruit juices are available from the local grocery stores.

Because the fructose is consumed prior to a meal, individual unit dose size packages are preferred over bulk packaging. Suitable dosage forms typically include tablet, caplet, lozenge, powder, crystal, fruit, syrup, candy and liquid. Examples of preferred dosage forms typically include crystalline fructose packaged in a sachet, fructose chewable tablets packaged in a roll, individually wrapped hard candies, an 8 fl. oz bottle of grape juice and one medium raw apple.

Typically, from about 1 to about 10 fructose doses are consumed prior to the meal, preferably from about 1 to about 5, more preferably from about 1 to 2 fructose doses are consumed prior to the meal. One knowledgeable in the art would be able to produce acceptable dosage forms by well known manufacturing procedures in the food and confectionery industry.

As noted above, the fructose dose is consumed from about 10 to about 90 minutes before a meal, preferably from about 15 to about 75 minutes before a meal, more preferably from about 30 to about 60 minutes before a meal.

A diabetic would typically practice the method of the invention 30 minutes prior to a meal, by consuming 2 hard candies that contain 5 gm of fructose each.

Numerous types of containers are readily available and know to one practicing the art. Convenience is the primary criteria for selecting the appropriate container depending on the dosage form. Examples of container types typically include packets or sachets which are typically manufactured of paper, foil and plastic film, and foil and plastic film coated paper; blister packs which are typically manufactured of paper, foil, plastic, plastic film; rolls or tubes which are typically manufactured of paper, foil, plastic, plastic film; ampoules which may be manufactured of plastic, reinforced paper and glass; and individual wrappers which are typically manufactured of paper, foil, plastic film.

Experiment I

The primary objective of this study was to determine the effects of the timing of fructose ingestion on the postprandial glycemic response of healthy nondiabetic adult subjects to instant mashed potatoes, a rapidly digested starch. A secondary objective was to evaluate the effects of an acute challenge of 50 g of carbohydrate from instant mashed potatoes ±10 g fructose on subjective gastrointestinal tolerance.

The study followed a double-blind crossover design in which subjects participated in four 2-hour meal tolerance tests on separate occasions. Subjects were randomly assigned to one of 24 treatment sequences. After an overnight fast, subjects consumed 50 g carbohydrate from instant mashed potatoes with or without 10 g supplemental fructose. The effects of the timing of fructose ingestion were evaluated by having the subjects consume 10 g fructose 60, 30, or 0 min before the instant mashed potato meal. A control meal tolerance test was given where subjects received no fructose.

To ensure that subjects had similar glycogen stores on the 4 test days, subjects were instructed to consume a high carbohydrate diet (minimum 150 g carbohydrate per day) for 3 days before each meal tolerance test and were also asked to avoid exercise 24 hours before the experiment. On the evening before each meal tolerance test, all subjects consumed a low-residue dinner consisting of one 8 fl oz (237 ml) can of chocolate Ensure Plus® (Ross Laboratories, Columbus, Ohio) with additional Honey Graham Crunch Ensure® Bars (Ross Laboratories, Columbus, Ohio) to provide one-third of each subject's individual daily caloric requirement as estimated by the Harris-Benedict equation multiplied by an activity factor of 1.3. Subjects were instructed to fast overnight, following their low-residue evening meal, during which they were only allowed to consume water and smoking was prohibited. On the morning of each meal tolerance test, body weight, body temperature, pulse rate and blood pressure were measured by standard procedures. A fasting finger-prick capillary blood sample was obtained and analyzed utilizing two methods of glucose determination. One sample was immediately analyzed for glucose with an Accu-Chek Blood Glucose Monitoring System (Roche Diagnostics, Indianapolis, Ind.). An additional sample was collected into a capillary tube containing EDTA for whole blood glucose analysis (within 30 min of collection) using a YSI analyzer (model YSI 2300 STAT PLUS, Yellow Springs Instruments, Yellow Springs, Ohio). This fasting sample was considered the −60 min time point. According to randomization, subjects then consumed 10 g fructose at −60 min, −30, or 0 min or no supplemental fructose (30 ml water at −60 min). The test meal (50 g carbohydrate from instant mashed potatoes) was given at time 0 and consumed within 10 min. Additional finger-prick capillary blood was obtained at −30, 0, 15, 30, 45, 60, 90 and 120 min postprandial. Subjects were allowed 8 fl oz water (240 ml) during each 2-hour test. Immediately following each trial, body temperature, pulse rate and blood pressure were measured. Subjects returned within 7 days for repeat analysis with the appropriate crossover treatment.

Using a questionnaire, subjects were asked to report the frequency and intensity of the following symptoms: nausea, cramping, distention, and flatulence for the 24-h period immediately following consumption of the test material. Intensity and frequency was set to a 100-mm line scale (0 representing "Absent" and 100 "Severe" and 0 representing "Usual" and 100 "More than usual," respectively). Subjects placed a single perpendicular slash mark across the 100 mm horizontal line to indicate their scores for each of these variables of frequency and intensity. A score of 5 or less was considered not physiologically meaningful.

All subjects were between 18 and 75 years of age, inclusively; were male or a non-pregnant female at least 6 weeks postpartum and nonlactating; were not currently receiving oral contraceptives; had a body mass index (BMI) between 20 and 28 kg/m$^2$; did not have diabetes mellitus or glucose intolerance (baseline serum glucose<110 mg/dl (6.11 mmol/L)); did not have a family history (first degree relatives) of diabetes mellitus or glucose intolerance; were free from active metabolic or gastrointestinal diseases that may interfere with nutrient absorption, distribution, metabolism, or excretion and had no known food allergies; had not had a recent (<3 months) infection, surgery or corticosteroid treatment and was not under a high level of stress; were willing to consume Ensure® Plus and Ensure® Bar(s) as the evening meal on the day prior to test; were willing to fast (10 hours) prior to testing and were willing to consume the product within a 10-min period; abstained from exercise 24 hours prior to testing and minimized activity during the test; were not taking daily medications (e.g., acetaminophen, salicylates, diuretics, etc.) that would interfere with nutrient absorption, metabolism, excretion or gastric motility; voluntarily signed an informed consent form prior to any participation in the study.

The products tested were instant mashed potatoes (Hungry Jack Mashed Potatoes; Pillsbury Company) and purified crystalline fructose (Wild Oats Market grocery; Columbus, Ohio). The composition of each test product is listed in Table 2 below.

TABLE 2

Composition of Products*

| Composition | Instant mashed potatoes per meal tolerance test serving | Fructose |
|---|---|---|
| Fat, g | 0 | 0 |
| Protein, g | 6 | 0 |
| Carbohydrate, g | 50 | 10 |
| fructose, g | 0 | 10 |

*Instant mashed potato (Hungry Jack Mashed Potatoes; Pillsbury Company) composition based upon nutrition facts label. Purified crystalline fructose (Wild Oats Market grocery; Columbus, OH) analysis completed by Ross Products Division of Abbott Laboratories.

The primary variable for this study was incremental peak plasma glucose response. Secondary variables included incremental area under the curve, time to peak glucose, glycemic index, and subjective gastrointestinal tolerance factors. Exploratory variables included absolute and incremental plasma glucose response at −30, 0, 15, 30, 45, 60, 90, and 120 min postprandial.

A total of 31 healthy nondiabetic (fasting plasma glucose value less than 110 mg/dl; American Diabetes Association, 1997) volunteers (thirteen men and eighteen women) were recruited. Subjects had a mean (±SE) age of 26±1 years (range: 20 to 41 years), weight of 66±3 kg (range: 45 to 96 kg), and body mass index of 23.3±0.6 kg/m$^2$ (range: 18.3 to 29.7 kg/m$^2$). Twenty were self-described as Caucasian, ten as Asian or Pacific Islander, and one as Latino. Subjects did not have active gastrointestinal or metabolic diseases, a first-degree family history of diabetes mellitus or glucose intolerance, recent infection, surgery or corticosteriod treatment. No subjects were receiving oral contraceptives.

Fasting plasma glucose concentration (measured at −60 min) was not different (P>0.05) among the treatments. Peak incremental change from baseline and incremental area under the curve for plasma glucose were lower (P<0.05) when subjects consumed 10 g fructose 60 or 30 min before the meal tolerance test compared to when subjects consumed fructose with the meal or when subjects did not consume any supplemental fructose. Time to peak glucose did not differ (P>0.05) between treatments. (Table 3)

TABLE 3

Time to peak glucose, peak incremental change from baseline in glucose, incremental area under the curve for glucose, and glycemic index

| | Time of fructose ingestion, min^ (Mean ± SEM) | | | |
|---|---|---|---|---|
| | −60 | −30 | 0 | none |
| Accu-Chek values | | | | |
| Incremental peak glucose (mg/dl)† | 51.6 ± 2.2 | 49.5 ± 2.5 | 65.7 ± 3.2 | 62.2 ± 3.2 |
| Time to peak (min) | 35 ± 1.3 | 36 ± 2.0 | 38 ± 1.9 | 41 ± 1.9 |
| Incremental AUC (mg · min/dl)† | 2398 ± 142 | 2329 ± 210 | 3059 ± 246 | 3199 ± 225 |
| Glycemic index‡ | 84.1 ± 6.6 | 80.2 ± 8.5 | 98.8 ± 6.2 | 100 |
| n | 31 | 31 | 31 | 31 |
| YSI values | | | | |
| Incremental peak glucose (mg/dl)† | 44.4 ± 2.0 | 39.9 ± 2.6 | 56.7 ± 3.0 | 52.4 ± 2.9 |
| Time to peak (min) | 33 ± 1.2 | 33 ± 1.5 | 37 ± 1.8 | 38 ± 1.7 |
| Incremental AUC (mg · min/dl)† | 2094 ± 132 | 1880 ± 189 | 2592 ± 213 | 2634 ± 206 |
| Glycemic index‡ | 89.6 ± 7.5 | 82.5 ± 10.6 | 107.1 ± 11.1 | 100 |
| n | 26 | 25 | 28 | 27 |

^Time of fructose ingestion relative to time of test meal consumption (instant mashed potatoes).
†Treatment effect, P < 0.001; −60 and −30 differ from 0 and none, P < 0.05.
‡Glycemic index = incremental AUC for treatment/incremental AUC for control (i.e., no supplemental fructose) × 100.

The postprandial glycemic excursion is graphically depicted in FIGS. 1 through 4. Consumption of 10 g fructose at −60 min increased (P<0.05) incremental change from baseline (i.e., the −60 min value) in plasma glucose at the −30 min time point compared to the other treatments. Similarly, consumption of 10 g fructose at −30 min increased (P<0.05) incremental change from baseline in plasma glucose at the 0 min time point compared to the 0-min time fructose ingestion treatment. At 15 min, subjects given fructose at −30 min had a higher (P<0.05) incremental change from baseline in plasma glucose compared to the control and 0-min time fructose ingestion treatment. Over the 30, 45 and 60 min time points, incremental change from baseline in plasma glucose tended to be lower for subjects when they consumed fructose −60 or −30 min relative to the meal tolerance test. The postprandial incremental change from baseline in plasma glucose did not differ (P>0.05) between treatments at 90 and 120 min. Consumption of fructose with the meal tolerance test had no effect on the postprandial glycemic response compared to the control.

The data in Table 4 documents the gastrointestinal tolerance of healthy nondiabetic adult subjects given an acute challenge of 50 g carbohydrate from instant mashed potatoes with or without 10 g supplemental fructose. Minimal effects on gastrointestinal symptoms (intensity and frequency of nausea, cramping, distention and flatulence) were noted for all treatments.

TABLE 4

Gastrointestinal tolerance for 31 subjects consuming 50 g carbohydrate from instant mashed potatoes ± 10 g fructose given at different times*

| | Time of fructose ingestion, min[†] | | | |
|---|---|---|---|---|
| | −60 | −30 | 0 | none |
| Intensity of | | | | |
| Nausea | 1 ± 0.3 | 1 ± 0.4 | 0 ± 0.2 | 3 ± 2.2 |
| Cramping | 1 ± 0.3 | 2 ± 1.6 | 3 ± 1.9 | 2 ± 1.3 |
| Distention | 1 ± 1.0 | 3 ± 1.5 | 1 ± 0.4 | 3 ± 1.8 |
| Flatulence | 3 ± 1.5 | 5 ± 1.7 | 1 ± 0.5 | 4 ± 1.7 |
| Frequency of | | | | |
| Nausea | 1 ± 0.3 | 1 ± 0.2 | 1 ± 0.2 | 4 ± 2.9 |
| Cramping | 4 ± 3.2 | 1 ± 0.2 | 7 ± 4.1 | 6 ± 3.6 |
| Distention | 1 ± 0.3 | 4 ± 1.9 | 1 ± 0.6 | 3 ± 1.7 |
| Flatulence | 3 ± 1.7 | 7 ± 2.9 | 3 ± 1.3 | 6 ± 3.1 |

*Mean ± SEM, n = 31. A score of 5 or less was considered not physiologically meaningful.
[†]Time of fructose ingestion relative to time of test meal consumption (instant mashed potatoes).

The results of the present study were surprising as they found that 10 g supplemental fructose when given with a meal glucose tolerance test (50 g carbohydrate from instant mashed potatoes) had no effect on the postprandial glycemic response. However, when 10 g of fructose were given 30 or 60 min before the meal tolerance test, fructose reduced the postprandial glycemic response.

I claim:

1. A method for blunting the postprandial glycemic response to a meal, said method comprising feeding a diabetic individual from about 2 grams to about 30 grams of a source of supplemental fructose from about 10 minutes to about 90 minutes prior to a meal, wherein the source of supplemental fructose is selected from the group consisting of liquid fructose, powder fructose and crystalline fructose, in a dosage form selected from the group consisting of sachet, tablet, caplet, lozenge, powder, syrup, and liquid.

2. The method according to claim 1 wherein about 5 grams to about 15 grams of said supplemental fructose source is fed to the individual about 15 minutes to about 75 minutes prior to a meal.

3. The method according to claim 2 wherein about 10 grams of said supplemental fructose source is fed to the individual about 30 minutes to about 60 minutes prior to a meal.

4. The method according to claim 1 wherein the supplemental fructose is fed to the individual about 30 minutes to about 60 minutes prior to a meal.

5. A method for modulating blood glucose, said method comprising feeding a diabetic individual from about 2 grams to about 30 grams of a source of supplemental fructose from about 10 minutes to about 90 minutes prior to a meal, wherein the source of supplemental fructose is selected from the group consisting of liquid fructose, powder fructose and crystalline fructose, in a dosage form selected from the group consisting of sachet, tablet, caplet, lozenge, powder, syrup, and liquid.

6. The method according to claim 5 wherein about 5 grams to about 15 grams of said supplemental fructose source is fed to the individual about 15 minutes to about 75 minutes prior to a meal.

7. The method according to claim 6 wherein about 10 grams of said supplemental fructose source is fed to the individual about 30 minutes to about 60 minutes prior to a meal.

8. The method according to claim 5 wherein the supplemental fructose is fed to the individual about 30 minutes to about 60 minutes prior to a meal.

9. A method for assisting a diabetic patient with managing their blood glucose levels, said method comprising feeding said diabetic patient from about 2 grams to about 30 grams of a source of supplemental fructose from about 10 minutes to about 90 minutes prior to a meal, wherein the source of supplemental fructose is selected from the group consisting of liquid fructose, powder fructose and crystalline fructose, in a dosage form selected from the group consisting of sachet, tablet, caplet, lozenge, powder, syrup, and liquid.

10. The method according to claim 9 wherein about 5 grams to about 15 grams of said supplemental fructose source is fed to the patient about 15 minutes to about 75 minutes prior to a meal.

11. The method according claim 10 wherein about 10 grams of said supplemental fructose source is fed to the patient about 30 minutes to about 60 minutes prior to a meal.

12. The method according to claim 9 wherein the supplemental fructose is fed to the patient about 30 minutes to about 60 minutes prior to a meal.

* * * * *